(12) United States Patent
Dunson, Jr. et al.

(10) Patent No.: US 8,512,979 B2
(45) Date of Patent: *Aug. 20, 2013

(54) SYSTEM AND PROCESS FOR BIOMASS TREATMENT

(75) Inventors: James B. Dunson, Jr., Newark, DE (US); Melvin P. Tucker, III, Lakewood, CO (US); Richard T. Elander, Evergreen, CO (US); Robert C. Lyons, Arvada, CO (US)

(73) Assignees: E I du Pont de Nemours and Company, Wilmington, DE (US); Alliance for Sustainable Energy LLC

( * ) Notice: Subject to any disclaimer, the term of this patent is extended or adjusted under 35 U.S.C. 154(b) by 578 days.

This patent is subject to a terminal disclaimer.

(21) Appl. No.: 12/705,683

(22) Filed: Feb. 15, 2010

(65) Prior Publication Data

US 2010/0178677 A1 Jul. 15, 2010

Related U.S. Application Data

(62) Division of application No. 11/402,464, filed on Apr. 12, 2006, now abandoned.

(60) Provisional application No. 60/670,437, filed on Apr. 12, 2005.

(51) Int. Cl.
*C12P 1/00* (2006.01)
*C12P 19/00* (2006.01)
*C12P 19/14* (2006.01)

(52) U.S. Cl.
USPC .................... 435/41; 435/72; 435/99; 127/37

(58) Field of Classification Search
USPC ................................. 435/41, 72, 99; 127/37
See application file for complete search history.

(56) References Cited

U.S. PATENT DOCUMENTS

| 4,136,207 A | 1/1979 | Bender |
| 4,186,658 A | 2/1980 | Brown |
| 4,257,818 A | 3/1981 | Regnault et al. |
| 4,407,955 A | 10/1983 | Muller et al. |
| 4,461,648 A | 7/1984 | Foody |
| 4,859,283 A | 8/1989 | Jayawant |
| 4,863,707 A | 9/1989 | McShea et al. |
| 5,008,473 A | 4/1991 | Breitkopt et al. |
| 5,037,663 A | 8/1991 | Dale |
| 5,192,673 A | 3/1993 | Jain et al. |
| 5,227,136 A | 7/1993 | Hanify et al. |
| 5,356,812 A | 10/1994 | Matsuyama et al. |
| 5,366,553 A | 11/1994 | Lair et al. |
| 5,705,369 A | 1/1998 | Torget et al. |
| 5,879,463 A | 3/1999 | Proenca |
| 5,916,780 A | 6/1999 | Foody |
| 5,981,270 A | 11/1999 | Roberts et al. |
| 6,013,494 A | 1/2000 | Nakamura et al. |
| 6,090,595 A | 7/2000 | Foody |
| 6,159,738 A | 12/2000 | Donnelly et al. |
| 6,176,176 B1 | 1/2001 | Dale et al. |
| 6,228,630 B1 | 5/2001 | Kofod et al. |
| 6,254,914 B1 | 7/2001 | Singh et al. |
| 6,358,716 B1 | 3/2002 | Bulthuis et al. |
| 6,358,717 B1 | 3/2002 | Blaschek et al. |
| 6,431,478 B1 | 8/2002 | Reed et al. |
| 6,514,733 B1 | 2/2003 | Emptage et al. |
| 6,777,207 B2 | 8/2004 | Kjeldsen et al. |
| 6,861,237 B2 | 3/2005 | Anderson et al. |
| 6,962,805 B2 | 11/2005 | Asakura et al. |
| 2003/0162271 A1 | 8/2003 | Zhang et al. |
| 2003/0170834 A1 | 9/2003 | Gatenby et al. |
| 2004/0016525 A1 | 1/2004 | Gervais |
| 2004/0231060 A1 | 11/2004 | Burdette et al. |
| 2005/0161038 A1 | 7/2005 | Pinatti et al. |
| 2005/0166812 A1 | 8/2005 | Noll et al. |
| 2005/0250192 A1 | 11/2005 | Shanmugam et al. |
| 2006/0003429 A1 | 1/2006 | Frost et al. |
| 2007/0029252 A1 | 2/2007 | Dunson et al. |
| 2007/0031918 A1 | 2/2007 | Dunson et al. |
| 2007/0259410 A1 | 11/2007 | Donaldson et al. |
| 2007/0292927 A1 | 12/2007 | Donaldson et al. |

FOREIGN PATENT DOCUMENTS

| EP | 0263515 A2 | 4/1988 |
| EP | 0332234 B1 | 9/1989 |
| EP | 136359 B1 | 4/1991 |
| EP | 0631980 A1 | 1/1995 |
| FR | 656385 A | 5/1929 |
| JP | 47004505 | 3/1972 |

(Continued)

OTHER PUBLICATIONS

Sheehan and Himmel. Enzymes, Energy, and the Environment: A Strategic Perspective on the U.S. Department of Energy's Research and Development Activities for Bioethanol. Biotechnol. Prog. 1999, 15, 817-827.*

Gusakov et. al., Kinetics of the Enzymatic Hydrolysis of Cellulose: 1. A Mathematical Model for a Batch Reactor Process, Enz. Microb. Technol., 1985, vol. 7:346-352.

Rye et. al., Bioconversion of Waste Cellulose by Using an Attrition Bioreactor, Biotechnol. Bioeng., 1983, vol. 25:53-65.

Lee et. al., Cellulose Hydrolysis Under Extremely Low Sulfuric Acid and High-Temperature Conditions, Appl. Biochem. Biotech., 2001, vol. 91-93:331-340.

Gusakov et. al., Enhancement of Enzymatic Cellulose Hydrolysis Using a Novel Type of Biorector with Intese Stirring Induced Byelectromagnetic Field, Appl. Biochem. Biotechnol., 1996, vol. 56:141-153.

(Continued)

*Primary Examiner* — Taeyoon Kim (57) ABSTRACT

A system including an apparatus is presented for treatment of biomass that allows successful biomass treatment at a high solids dry weight of biomass in the biomass mixture. The design of the system provides extensive distribution of a reactant by spreading the reactant over the biomass as the reactant is introduced through an injection lance, while the biomass is rotated using baffles. The apparatus system to provide extensive assimilation of the reactant into biomass using baffles to lift and drop the biomass, as well as attrition media which fall onto the biomass, to enhance the treatment process.

10 Claims, 2 Drawing Sheets

(56) References Cited

FOREIGN PATENT DOCUMENTS

| | | |
|---|---|---|
| JP | 47038995 | 10/1972 |
| JP | 51006237 | 1/1976 |
| JP | 51019037 | 2/1976 |
| JP | 54032070 | 3/1979 |
| JP | 54037235 | 3/1979 |
| JP | 56008596 | 1/1981 |
| JP | 56010035 | 2/1981 |
| JP | 57150381 | 9/1982 |
| JP | 859681 | 3/1991 |
| JP | 3207079 | 9/1991 |
| JP | 3723579 | 9/2005 |
| JP | 3899572 | 1/2007 |
| WO | 94/03646 A1 | 2/1994 |
| WO | 03/078644 A2 | 9/2003 |
| WO | 2004/018645 A2 | 3/2004 |
| WO | 2004/081185 A1 | 9/2004 |
| WO | 2007/041269 A2 | 4/2007 |
| WO | 2007/050671 A2 | 5/2007 |

OTHER PUBLICATIONS

Teixeira et. al., Alkaline and Peracetic Acid Pretreatments of Biomass for Ethanol Production, Appl., Biochem. Biotech., 1999, 77-79, 19-34.

Gould, Alkaline Peroxide Delignification of Agricultural Residues to Enhance Enzymatic Saccharification, Biotech. Bioeng., 1983, vol. 26:46-52.

Curreli et. al., Complete and efficient enzymic hydrolysis of pretreated wheat straw, Process Biochem., 2002, vol. 37:937-941.

Teymouri et. al., Optimization of the Ammonia Fiber Expolsion (AFEX) Treatment Parameters for Enzymatic Hydrolysis of Corn Stover, Bioresource Tech., 2005, vol. 96:2014-2018.

Lynd et. al., Microbial Cellulose Utilization: Fundamentals and Biotechnology, Microbiol. Mol. Biol. Rev., 2002, vol. 66:506-577.

Enzyme Nomenclature. Recommendaation 1992, Supplement: Corrections and Additions, Eur. J. Biochem, 1994, vol. 223:1-5.

Enzyme Nomenclature. Recommendaation 1992, Supplement 2: Corrections and Additions, E Ur. J. Biochem., 1995, vol. 232:1-6.

Enzyme Nomenclature. Recommendations 1992, Supplement 3: Corrections and Additions, Eur. J. Biochem., 1996, vol. 237:1-5.

Enzyme Nomenclature. Recommendations 1992, Supplement 4:Corrections and Additions, Eur. J. Biochem., 1997, vol. 250:1-6.

Nomenclature Committee of the International Union of Biochemistry and Molecular Biology (NC-IUBMB), Eur. J. Biochem., 1999, vol. 264:610-650.

H. Hagino, Control Mechanisms in Aromatic Amino Acid Biosynthesis and the Amino Acid Production, Arg. Chem. Soc., Japan, 1976, vol. 50:R79-R87.

Aden et al., Biofuels for Sustainable Transportation, National Renewable Energy Laboratory Report TP-510-32438, 2000.

Lloyd et al., Application of a Depolymerization Model for Predicting Thermochemical Hydrolysis of Hemicellulose, Appl. Biochem. & Biotechnol., 2003, vol. 105:53-57.

Lloyd et al., Combined Sugar Yields for Dilute Sulfuric Acid Pretreatment of Corn Stover Followed by Enzymatic Hydrolysis of the Remaining Solids, Bioresource Technol., 2005, vol. 96:1967-1977.

In et al., Chemical Engineer's Handbook, 5th Edition, 1973, Chapter 4, McGraw-Hill NY, (Book Not Included).

Tay et al., Production of L (+)-Lactic Acid From Glucose and Starch by Immobilized Cells of *Rhizopus oryzae* in a Rotating Fibrous Bed Bioreactor, Biotechnol. Bioeng., 2000, vol. 80:1-12.

Niu et al., Benzene-Free Synthesis of Adipic Acid, Biotechnol. Prog., 2002, vol. 18:201-211.

Cheryan et al., Production of Acetic Acid by *Clostridium thermoaceticum*, Adv. Appl. Microbiol., 1997, vol. 43:1-33.

Freer, Acetic Acid Production by Dekkera/Brettanomyces Yeasts, World J. Microbiol. Biotechnol., 2002, vol. 18:271-275.

Lin et al., Metabolic Engineering of Aerobic Succinate Production Systems in *Escherichia coli* to Improve Process Productivity and Achieve the Maximum Theoretical Succinate Yield, Metab. Eng., 2005, vol. 7:116-127.

Li et al., Appl. Efficient Pyruvate Production by a Multi-Vitamin Auxotroph of *Torulopsis glabrata*? Key Role and Optimization of Vitamin Levels, Appl. Microbiol. Biotechnol., 2001, vol. 55:680-685.

Yokota et al., Pyruvic Acid Production by an F-Atpase-Defective Mutant of *Escherichia coli* W1485LIP2, Biosci. Biotech. Biochem., 1994, vol. 58:2164-2167.

Suwannakham et al., Enhanced Propionic Acid Fermentation by Propionbacterium Acidpropionici Mutant Obtained by Adaptation in a Fibrous-Bed Bioreactor, Biotechnol. Bioeng., 2005, vol. 91:325-337.

Wu et al., Extractive Fermentation for Butyric Acid Production From Glucose by *Clostridium tyrobutyricum*, Biotechnol. Bioeng., 2003, vol. 82:93-102.

Janssen, Propanol as an End Product of Threonine Fermentation, Arch Microbiol., 2004, vol. 182:482-486.

Anantassiadis et al., Process Optimization of Continuous Gluconic Acid Fermentation by Isolated Yeast-Like Strains of *Aureobasidium pullulans*, Biotechnol. Bioeng., 2005, vol. 91:494-501.

Singh et al., Optimization of Fermentation Conditions for Gluconic Acid Production by a Mutant of *Aspergillus niger*, Indian J. Exp. Biol., 2001, vol. 39:1136-1143.

Elfari et al., A Gluconobacter Oxydans Mutant Converting Glucose Almost Quantitatively to 5-Keto-D-Gluconic Acid, Appl. Microbiol., Biotech., 2005, vol. 66:668-674.

Reddy et al., Enhanced Production of Itconic Acid From Corn Starch and Market Refuse Fruit by Genetically Manipulated *Aspergillus terreus* SKR10, Bioresour. Technol., 2002, vol. 85:69-71.

Ui-Haq et al., Optimization OG Nitrogen for Enhanced Citric Acid Productivity by a 2-Deoxy D-Glucose Resistant Culture of *Aspergillus niger* NGD-280, Bioresour. Technol., 2005, vol. 96:645-648.

Mussatto et al., Xylitol Production From High Xlose Concentration: Evaluation of the Fermentation in Bioreactor Under Different Stirring Rates, J. Appl. Microbiol., 2003, vol. 95:331-337.

Gorenflo et al., Development of a Process for the Biotechnological Large-Scale Production of 4-Hydroxyvalerate-Containing Polyesters and Characterization of Their Physical and Mechanical Properties, Biomacromolecules, 2001, vol. 2:45-57.

Ui et al., Production of L-2,3-Butanediol by a New Pathway Constructed in *Escherichia coli*, Leet. Appl. Microbiol., 2004, vol. 39:533-537.

Okamoto et al., Development of an Industrially Stable Process for L-Threonine Fermentation by an L-Methionine-Auxotrophic Mutant of *Escherichia coli*, J. Biosci. Bioeng., 2000, vol. 89:79-87.

Kumar et al., Effect of Cysteine on Methionine Production by a Regulatory Mutant of *Corynebacterium lilium*, Bioresour. Technol., 2005, vol. 96:287-294.

Durre, New Insights and Novel Developments in Clostridial Acetone/Butanol/Isopropanol Fermentation, Appl. Microbiol. Biotechnol., 1998, vol. 49:639-648.

Groot et al., Technologies for Butanol Recovery Intergrated With Fermentations, Process Biochem., 1992, vol. 27:61-75.

Nakayama et al., Fermentative Production of L-Arginine, Arg. Biol. Chem., 1972, vol. 36:1675-1684.

Elshafei et al., The Saccharification of Corn Stover by Cellulase From *Penicillium funiculosum*, Bioresource Tech., 1991, vol. 35:73-80.

Kim et al., Pretreatment and Fractionation of Corn Stover by Ammonia Recycle Percolation Process, Bioresource Technology, 2005, vol. 96:2007-2013.

R.H. Perry et al., Chemical Engineer's Handbook, 5th Edition, Chapter 4, 1973 (Book Not Included).

Kirk-Othmer Encyclopedia of Chemical Technology, 4th Edition, 1997 (Book Not Included).

Teymouri et al., Optimization of the Ammonia Fiber Expolsion (AFEX) Treatment Parameters for Enzymatic Hydrolysis of Corn Stover, Bioresource Tech., 2005, vol. 96:2014-2018.

Mosier et al., Features of Promising Technologies for Treatment of Lignocellulosic Biomass, Bioresource Technology, 2005, vol. 96:673-686.

K.N. Joblin et al., Fermentation of Barley Straw by Anaerobic Rumen Bacteria and Fungi in Axenic Culture and in Co-Culture With Methanogens, Letters in Applied Microbiology, 1989, vol. 9:195-197.

Kurakake et al., Pretreatment With Ammonia Water for Enzymatic Hydrolysis of Corn Husk, Bagasse and Switchgrass, Applied Biochemistry and Biotechnology, 2001, vol. 90:251-259.

Taylor et al., Corn Milling Pretreatment With Anhydrous Ammonia, Applied Biochemistry and Biotechnology, 2003, vol. 104:141-148.

Barron et al., Ethanol Production by *Kluyveromyces marxianus* IMB3 During Growth on Straw-Supplemented Whiskey Distillery Spent Wash at 45 Degrees C., Bioprocess Engineering, 1997, vol. 17:383-386.

Iyer et al., Ammonia Recycled Percolation Process for Pretreatment of Herbaceous Biomass, Applied Biochemistry and Biotechnology, 1996, vol. 57-58:121-132.

D. Ben-Ghedalia et al., The Effect of Chemical Pretreatments and Subsequent Enzymatic Treatments of the Organic Matter Digestibility In Vitro of Wheat Straw, Nutrition Reports International, 1979, vol. 19:499-505.

A.C. Waiss et al., Improving Digestibility of Straws for Ruminant Feed by Aqueous Ammonia, Journal of Animal Science, 1972, vol. 35:109-112.

N. J. Cao et al., Ethanol Production From Corn Cob Pretreated by the Ammonia Steeping Process Using Gentically Engineered Yeast, Biotechnology Letters, vol. 18:1013-1018, 1996, XP008067477.

Kim et al., Pretreatment of Corn Stover by Soakingin Aqueous Ammonia, Applied Biochemistry & Biotechnology, 2005, vol. 121:1119-1131.

Cao et. al., Production of 2, 3 Butanediol From Pretreated Corn Cob by *Klebsiella oxytoco* in the Presence of Fungal Cellulase, Applied Biochemistryand Biotechnology, 1997, vol. 63-65:129-139.

S. K. Rhu and J. M. Lee, Bioconversion of Waste Cellulose by Using an Attrition Bioreactor, Biotechnology and Bioengineering, 1983, vol. 25: 53-65.

International Search Report Dated Sep. 1, 2006, International Application No. PCT/US/2006/014147, International Filing Date: Apr. 12, 2006, 3 Pages.

U.S. Appl. No. 60/847,813, filed Sep. 28, 2006, Viitanen et al.

U.S. Appl. No. 60/847,856, filed Sep. 28, 2006, Viitanen et al.

\* cited by examiner

FIG. 1

SYSTEM AND PROCESS FOR BIOMASS TREATMENT

This application claims the benefit of U.S. Provisional Application No. 60/670,437, filed Apr. 12, 2005.

STATEMENT OF GOVERNMENT RIGHTS

This invention was made with United States government support under Contract No. 04-03-CA-70224 awarded by the Department of Energy. The government has certain rights in this invention.

FIELD OF THE INVENTION

A system including an apparatus for treatment of biomass, including pretreatment as well as saccharification, is provided. Also processes for pretreating and saccharifying biomass at high dry weight of biomass in a biomass mixture using the system are provided. In addition, methods for optimizing biomass treatment processes are provided.

BACKGROUND OF THE INVENTION

Cellulosic and lignocellulosic feedstocks and wastes, such as agricultural residues, wood, forestry wastes, sludge from paper manufacture, and municipal and industrial solid wastes, provide a potentially large renewable biomass feedstock for the production of chemicals, plastics, fuels and feeds. Cellulosic and lignocellulosic feedstocks and wastes, composed of carbohydrate polymers comprising cellulose, hemicellulose, glucans and lignin are generally treated by a variety of chemical, mechanical and enzymatic means to release primarily hexose and pentose sugars, which can then be fermented to useful products. These treatments vary in complexity and efficiency. Further, there are many ongoing efforts to identify new commercially robust processes and to optimize known processes to generate useful fermentative products from cellulosic and lignocellulosic feedstocks.

In order to be an economically competitive process, a commercial process for the production of fermentable sugars from a renewable resource biomass requires the hydrolysis of carbohydrates in lignocellulosic biomass to provide high yields of sugars at high concentrations, using low amounts of chemicals, to produce a source of fermentable sugars with low toxicity toward fermentative organisms that convert sugars to value-added chemicals and fuels.

In order to carry out these processes, a variety of apparatuses have been employed for different types of biomass, as well as for different treatments, including small-scale process development and some large-scale production equipment. Some types of apparatuses that have been used include a batch-stirred reactor (Gusakov and Sinitsyn, (1985) Enz. Microb. Technol. 7:346-352), a continuous flow stirred reactor (U.S. Pat. No. 4,257,818), an attrition reactor (Ryu and Lee (1983) Biotechnol. Bioeng. 25:53-65), an extrusion reactor (U.S. Pat. No. 6,176,176), the NREL shrinking bed reactor (Lee et al. (2001) Appl. Biochem. Biotech. 91-93: 331-340), and a reactor with intensive stirring induced by an electromagnetic field (Gusakov et al. (1996) Appl. Biochem. Biotechnol., 56:141-153).

In particular, a reactor that is capable of providing means for efficient biomass pretreatment and/or saccharification at a high dry weight of biomass in a mixture is needed.

There remains a need for a simple, yet effective apparatus for use in biomass treatment processes, which may be used in a small-scale format for testing process conditions, with mechanisms for sampling that mimics operation in a large commercial scale. Moreover, there is an unmet need for commercially robust processes and equipment to carry out such processes, including saccharification at a high dry weight of biomass in a biomass mixture.

SUMMARY OF THE INVENTION

In one embodiment, the present invention provides a system including an apparatus for batch processing biomass comprising:
   a) an apparatus comprising:
      i) a cylindrical reaction vessel with an opening on at least one end;
      ii) one or more baffles attached to the interior of said vessel;
      iii) attrition media comprising pellets free-floating in the interior of the reaction vessel;
      iv) a cover for said vessel open end comprising one or more ports; and
      v) an injection lance comprising means for delivering a processing reactant, wherein said means is an injection lance extending the length of the reaction vessel and connecting to a first port in the cover of iv); and
   b) means for rotating the baffles of the vessel.

In another embodiment, the present invention provides a process for treating biomass comprising:
   a) introducing biomass to the reaction vessel of the apparatus of claim 1;
   b) introducing a processing reactant to the reaction vessel; and
   c) assimilating said processing reactant into said biomass by rotating the baffles of the reaction vessel whereby the baffles lift and drop the attrition media.

In another embodiment, the present invention provides a process for treating biomass comprising:
   a) pretreating biomass in the reaction vessel of the apparatus of claim 1, producing pretreated biomass;
   b) adjusting the temperature and pH of the pretreated biomass of a) in the reaction vessel; and
   c) saccharifying the adjusted pretreated biomass of b) in the reaction vessel.

In yet another embodiment, the present invention provides a method for optimizing a treatment process comprising:
   a) introducing biomass to the reaction vessel of the apparatus of claim 1;
   b) varying treatment conditions in the reaction vessel;
   c) sampling the treated biomass via said one or more ports under said varying treatment conditions; and
   d) testing said samples to determine optimal treatment conditions for processing biomass.

DETAILED DESCRIPTION OF THE INVENTION

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention provides a system including an apparatus used in biomass treatment processes, as well as processes for biomass treatment and methods for optimizing a treatment process that are carried out in the apparatus. The design of the system provides extensive distribution of a reactant by spreading the reactant over the biomass as the reactant is introduced or as the reactor is run. The system functions to provide extensive assimilation of the introduced reactant into biomass to enhance the treatment process. These features allow treatment at a high dry weight of biomass in a biomass mixture.

Definitions

In this disclosure, a number of terms are used. The following definitions are provided:

The term "fermentable sugar" refers to oligosaccharides and monosaccharides that can be used as a carbon source by a microorganism in a fermentation process.

The term "lignocellulosic" refers to a composition comprising both lignin and cellulose. Lignocellulosic material may also comprise hemicellulose.

The term "cellulosic" refers to a composition comprising cellulose.

By "dry weight" of biomass is meant the weight of the biomass having all or essentially all water removed. Dry weight is typically measured according to American Society for Testing and Materials (ASTM) Standard E1756-01 (Standard Test Method for Determination of Total Solids in Biomass) or Technical Association of the Pulp and Paper Industry, Inc. (TAPPI) Standard T-412 om-02 (Moisture in Pulp, Paper and Paperboard).

The term "saccharification" refers to the production of fermentable sugars from polysaccharides.

The term "pretreated biomass" means biomass that has been subjected to pretreatment prior to saccharification.

"Biomass" refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. According to the invention, biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from processing of grains, trees, branches, roots, leaves, wood chips, sawdust, shrubs and bushes, vegetables, fruits, flowers and animal manure. In one embodiment, biomass that is useful for the invention includes biomass that has a relatively high carbohydrate value, is relatively dense, and/or is relatively easy to collect, transport, store and/or handle.

In one embodiment of the invention, biomass that is useful includes corn cobs, corn stover and sugar cane bagasse.

An "aqueous solution comprising ammonia" refers to the use of ammonia gas ($NH_3$), compounds comprising ammonium ions ($NH_4^+$) such as ammonium hydroxide or ammonium sulfate, compounds that release ammonia upon degradation such as urea, and combinations thereof in an aqueous medium.

The term "treatment" refers to a process of a reactant acting on a material wherein the physical and/or chemical properties of the material are altered.

The term "reactant" refers to a composition that is able to alter the physical and/or chemical properties of a target material under conditions used in a treatment process.

An "enzyme consortium" for saccharification is a combination of enzymes that are able to act on a biomass mixture to produce fermentable sugars. Typically, a saccharification enzyme consortium may comprise one or more glycosidases; the glycosidases may be selected from the group consisting of cellulose-hydrolyzing glycosidases, hemicellulose-hydrolyzing glycosidases, and starch-hydrolyzing glycosidases. Other enzymes in the saccharification enzyme consortium may include peptidases, lipases, ligninases and feruloyl esterases.

Biomass Treatment System

Figure 1:
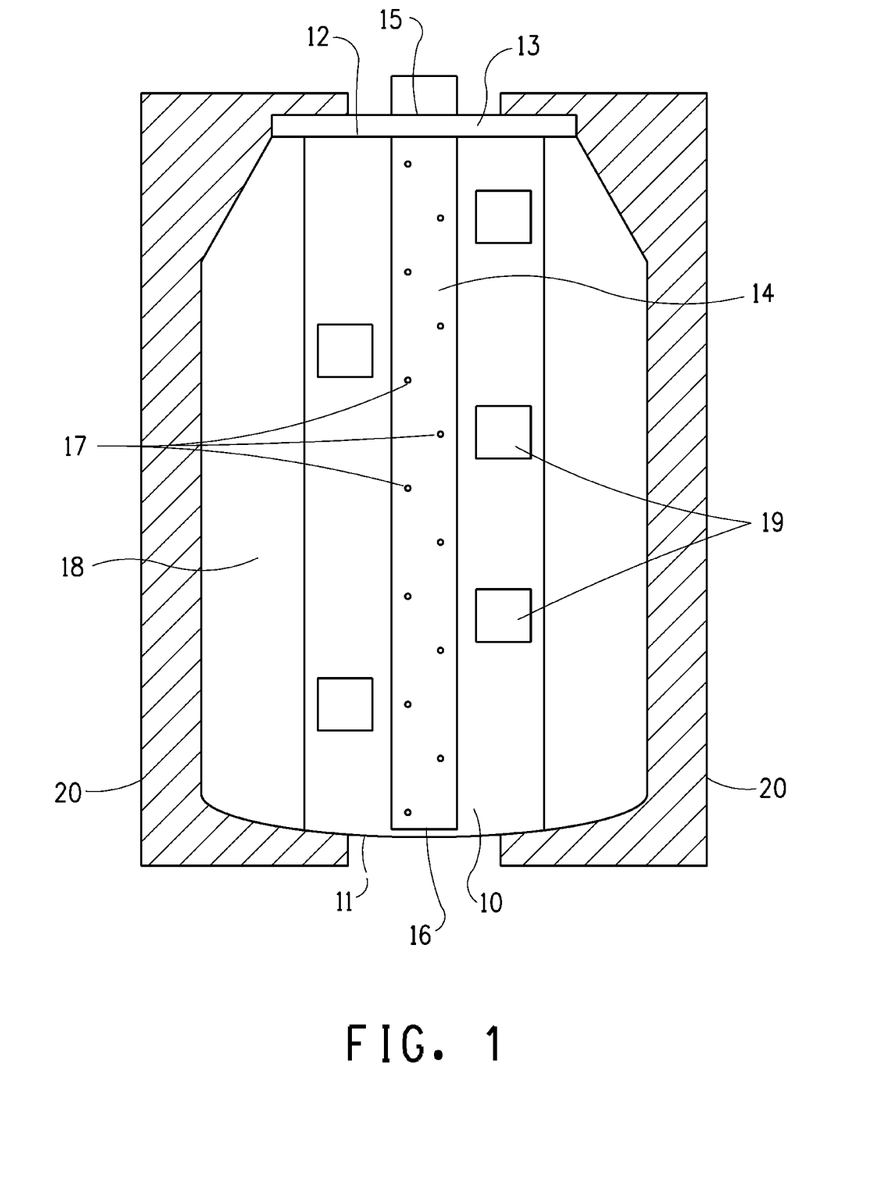
FIG. 1 shows a schematic representation of an embodiment of the biomass treatment system.

The present biomass processing system may best be understood by making reference to the schematic drawing in FIG. 1, which shows one embodiment of the system. The apparatus of the system comprises a cylindrical reaction vessel (10) having one closed end (11), and one open end (12). A removable cover (13) fits onto the open end, and may be securely fastened to the vessel open end. In the cover is at least one port. An injection lance (14) extends through the port, which is in the center of the cover (15), into the reaction vessel. The injection lance is a tube extending from the port through the longitudinal center of the cylindrical reaction vessel. The end of the injection lance that is distal from the port (16) is sealed. The injection lance has holes along its length that are arranged in a V-shape (17). These holes allow the escape of contents from inside the injection lance into the reaction vessel in an upward direction at about 10 o'clock and 2 o'clock. In addition, a vacuum source may be applied through the port to which the lance is connected, thereby creating a vacuum inside the vessel. Attached to the inside surface of the reaction vessel are baffles (18) which extend into the open space in the vessel, and do not touch the injection lance. In the interior of the reaction vessel are free-floating attrition media (19). The apparatus is placed horizontally on rollers (20) that are used to rotate the reaction vessel in the biomass processing system.

During biomass processing, the apparatus is maintained in a horizontal position and a means for rotating the baffles of the reaction vessel around the longitudinal axis of the vessel is applied to form a system for biomass processing. The baffles may be attached to the inside surface of the reaction vessel wall, in which case the whole vessel is rotated. Alternatively, the baffles may be attached to a sleeve type of surface on the inside of the reaction vessel, in which case the vessel itself is stationary while the sleeve rotates. Rotating the vessel or the sleeve may be accomplished by any method that provides for rotation. For example, to rotate the vessel it may be placed on external rollers, belts, wheels, trunnion bearings, or other rolling motion-inducing platforms. The apparatus may be housed in a reactor that imparts rotation to the vessel, or the rotation mechanism may be integrated with the apparatus. There may be a drive shaft extending through the vessel that is attached either to the vessel wall or to the sleeve for applying rotation. The speed of rotation may vary depending on the specific treatment process being used and the size of the apparatus. The rotation speed is sufficient to promote cascading of attrition media, as described herein below, and can readily be determined by one skilled in the art.

The cover for the open end of the reaction vessel may be secured to the vessel by means known in the art such as with screws, clamps, bars, dogs, or other fastners. The reaction vessel may be open at both ends, with a cover for each end. The port or ports in the cover (or both covers, if there is one at each end) are openings for access to the interior of the reaction vessel. A port may be a site for attachment of internal equipment such as the lance, and/or of external equipment such as a vacuum, or gas injection apparatus. Attachment of the external equipment may be temporary, only at times when needed during the treatment process, or permanent. Thus a port may have a connector, as well as a cover to close the port when not in use. Conventional connectors are used for joining to the port(s) in the cover(s), including a branched connector and a rotary joint. A port may also be an opening in the cover to provide access to the interior, such as for taking samples or releasing pressure, that itself may have a cover.

For biomass processing, the temperature of the apparatus is brought to the desired temperature and controlled. Control of the apparatus temperature may be accomplished by any method whereby heat is applied, such as by applying a heating jacket, injecting hot gas through the injection lance or through another port, flammable gas firing, or using waste flue gas heat from a boiler. Alternatively the apparatus may be housed in an oven, oil bath, or other type of reactor that provides heat to the apparatus. The temperature internal to the apparatus may be assessed by inserting a temperature measurement device, such as a thermocouple, through the port in the cover that is connected to the injection lance, and down the injection lance. By inserting the temperature measurement device halfway down the injection lance, the temperature at the approximate center of the reaction vessel may be determined. Cooling of the vessel may be imposed by methods such as applying ice or another coolant in a cooling jacket, passing cool gas through the injection lance, placing the reactor in a coolant bath, or cooling (refrigerating) an external box that the reaction vessel sits in. This may be done by an external mechanism, or by a mechanism of the apparatus.

The injection lance provides a means for introducing and distributing solutions or gases along the length of the reaction vessel. For example, nitrogen, $CO_2$, steam, processing reactant(s), and pH adjusting solution may be introduced through the injection lance. Processing reactants that are introduced through the injection lance may be preheated prior to injection, using any method known to one skilled in the art. For example, reactant heating may be accomplished by passing the processing reactant through a heating coil which is connected to the injection lance through the center port in the cover. The heating coil is immersed in a heated water bath, which is maintained at a temperature desirable for heating the processing reactant.

A vacuum may be applied to the reaction vessel of the apparatus through a port in the cover. A vacuum source may be connected to a port in the cover, typically the port that is connected to the injection lance. A branched connector or rotary joint provides connection for both the vacuum and access for reactant to the injector lance. A vacuum may be used to aid the infiltration of a processing reactant into biomass in the reactor vessel. By applying a vacuum to the vessel containing biomass, air may be evacuated from the biomass, allowing better penetration of the processing reactant when it is added. Also air in the reactor may be replaced with an inert atmosphere such as $N_2$ or Argon. A vacuum may be applied to help cool the contents of the reaction vessel, when a process is used that is amenable to evaporative cooling. Gases created during a biomass treatment process may be recovered by applying a vacuum and using a vent condenser. A vacuum source and a vent condenser may be attached to a port in the cover, such that vapors pass through the port and into the condenser. Condensed, recovered processing reactants, such as ammonia, may be reused in later biomass treatment processes. Removing ammonia, when used in pretreatment processing, lowers the pH of the pretreated biomass and thus saves on chemicals needed to neutralize the pretreated biomass to a pH optimal for enzymatic saccharification and biocatalyst fermentation. The lower chemical use also improves subsequent fermentation by lowering the salt load in contact with the microorganism, thus improving yield and productivity.

The reaction vessel of the apparatus may also be pressurized by injection through a port in the cover. For example, a $CO_2$ source may be connected to the port in the cover that is connected to the injection lance, and the $CO_2$ is injected, for example, to release a vacuum inside the reaction vessel, to reduce the pH, and/or to otherwise promote the biomass treatment process. A branched connector may serve for connection of the $CO_2$ source, a vacuum source, and access for reactant to the injection lance all through the same port.

Baffles attached to an inside surface in the reaction vessel may be in any form, number, and arrangement that promote the assimilation of processing reactant into the biomass when in the presence of attrition media (described herein below). The attrition media and biomass are lifted by the baffles as the baffles rotate around the bottom of the vessel, then slide off the baffles as they rotate around the top of the vessel. The baffles may extend in a perpendicular orientation to the inside surface, or they may be angled, with an angle that allows the lifting and then sliding off, or cascading, of the media. Baffles may run the length of the reactor vessel uninterrupted, or partial reactor length baffles may be placed in a line, or offset to each other. The baffles extend into the vessel interior forming a surface that is wide enough to lift the attrition media and narrow enough that the attrition media will readily slide off as the baffles move towards the top of the vessel. It will be understood to one skilled in the art that a variety of baffle forms, positioning, and number will be effective in cascading the attrition media and biomass as the baffles rotate to promote assimilation of processing reactant into the biomass, and that different arrangements will be optimal in different sized reaction vessels.

The apparatus is made from a generally non-corrosive material that will withstand pressures, temperatures, and processing reactants that are commonly used in biomass treatment processes. Examples of non-corrosive materials include stainless steel, Hastelloy®, ceramics, Inconel®, duplex stainless steel, zirconium and carbon steel. Different biomass treatment processes are carried out at temperatures ranging between −10° C. and about 220° C., with typical temperatures ranging between 4° C. and 170° C. Also biomass treatment processes may be carried out at temperatures ranging between room temperature (about 25° C.) and about 170° C. Pressures used in biomass treatment processes generally range between atmospheric and about 1200 kPa, with typical pressures ranging between atmospheric and about 310 kPa, and more typically between about atmospheric and 138 kPa. The materials used in a specific embodiment of the apparatus are those that withstand the conditions of the specific biomass treatment process to be used, as is well known to one skilled in the art. In one embodiment, a particularly suitable material for the reaction vessel is stainless steel of schedule 10 thickness that may be used with pressures between atmospheric and about 310 kPa, and temperatures up to about 145° C. Alternatively, the apparatus may be made of other materials that withstand higher temperatures and pressures, as well as highly corrosive process reactants such as strong acids. These more harsh biomass treatment conditions include temperatures up to about 220° C., with pressures up to about 1216 kPa, and strong acid reactants such as sulfuric acid. When using these process conditions, materials such as Hastelloy® and zirconium would be effective.

The diameter of the reaction vessel is large enough that the vessel can encompass the injection lance and baffles, as well as having room for attrition media to freely cascade as the baffles rotate. The reaction vessel may have an inner diameter of about 10 cm, with a typical inner diameter being at least about 15 cm, and may be scaled up further, including to a commercial size.

Figure 2A:
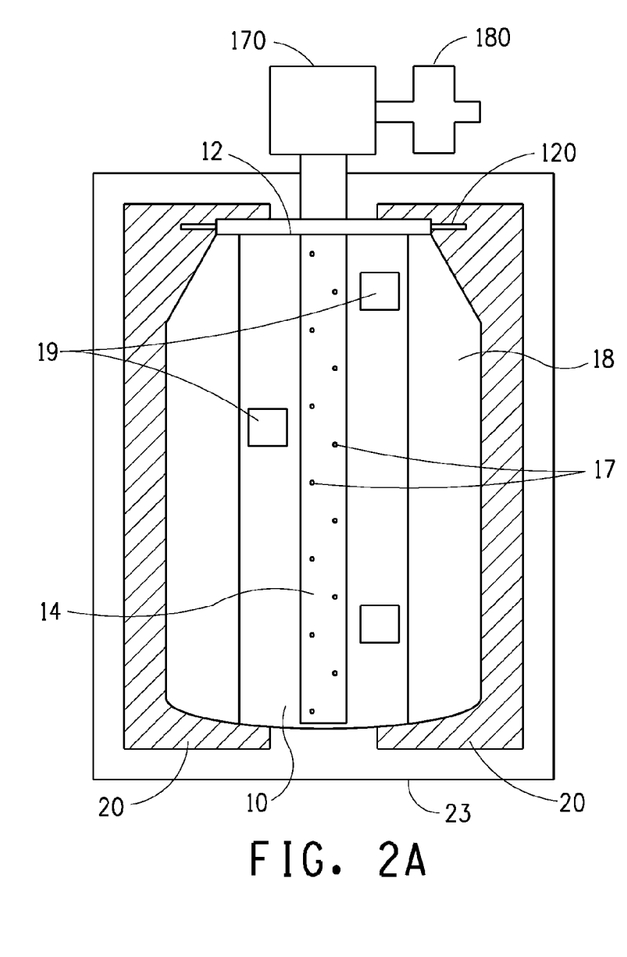
FIG. 2A shows a detailed drawing of an embodiment of the biomass treatment system. 2B shows a drawing of the reaction vessel cover.
Figure 2B:
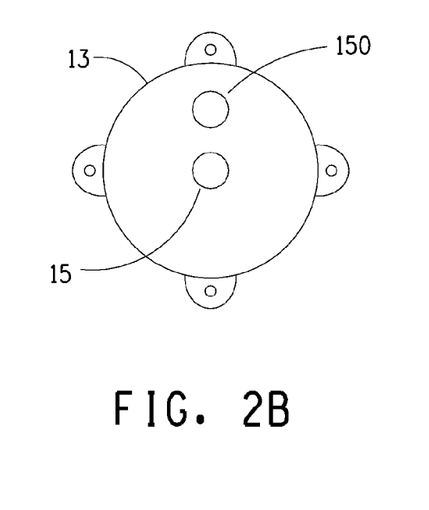

Attrition media are introduced into the apparatus and are free floating in the reaction vessel. Attrition media are added such that less than about 10% of the volume of the reaction vessel is occupied by the attrition media. Typically the attrition media occupy between about 3% and about 7% of the volume of the reaction vessel. The attrition media may be of different shapes and sizes and are used in different numbers, depending on the size of the reaction vessel. The appropriate attrition media, in size, shape, number, and composition for use in a specific embodiment of the apparatus, may be determined by one skilled in the art. Particularly useful are pellets such as cylinders made from heavy, dense material with a hard, non-porous, chip-resistant surface that is erosion resistant. Attrition media are available commercially, for example, from E. R. Advanced Ceramics (East Palestine, Ohio). As the baffles rotate, the attrition media are lifted by the baffles and then fall onto the biomass. The speed at which the baffles turn is adjusted such that the media undergo this cascading motion, rather than sliding down the vessel wall as occurs at too low a speed, or remaining next to the vessel wall as occurs at too high a speed. Without wishing to be bound by theory, it is thought that the attrition media landing on the biomass provide a squeezing pressure, which results in exuding of liquid that includes a mixture of processing reactant and solubilized biomass components. Bulk liquid then replaces the spent exuded liquid. Lifting of the weight of the attrition media from the biomass, as the baffles rotate, allows expansion of the biomass wherein the processing reactant mixture infiltrates into the biomass. The repetition of this squeezing from and infiltrating into the biomass of the processing reactant mixture creates a pumping action. Pumping of reactant mixture into and out of the biomass is a specialized type of mechanical mixing process that promotes assimilation of reactant into the biomass, and thereby enhances the biomass treatment process. This exchange of liquid allows higher concentration of reactants to be exchanged in the pores for depleted liquid that has already reacted in the pores of the biomass The following description of one embodiment of the present apparatus is not meant to be limiting, but to provide one particularly suitable apparatus structure. In one embodiment, as shown in FIG. 2, the apparatus has an approximately 9 L capacity in a reaction vessel (10) that is 51 cm long with an inner diameter of 15 cm. It is fabricated from 304 stainless steel pipe and fittings. The open end of the vessel (12) is 10 cm in diameter, with 4 equally spaced cover attachment sites (120) each extending 2.54 cm outward from the opening. The cover (13) is a circular plate that is 15.2 cm in diameter. There are two ports in the cover, a first port in the center (15) and a second port between the center and one edge (150), each 1.9 cm in diameter. The injection lance (14) extends through the center port in the cover and is connected to a rotary joint (170). There is a branched connector (180) attached to the rotary joint. The injection lance is made of stainless steel tubing of 0.64 cm diameter. The holes in the lance (17) are 0.165 cm in diameter, and are located at 2.54 cm intervals in a V pattern. The angle between the lines of holes is about 120°. There are two lines of holes, with the holes in a single line located 5.1 cm apart, and the holes in the 2 lines being offset by 2.54 cm, so effectively, there is a hole every 2.54 cm on alternating sides of the lance. The second port in the cover provides access for taking samples and adding reagents without removing the cover. There are four baffles (18) that each run the length of the reaction vessel wall, to which they are attached, and extend 3.8 cm from the inner vessel wall, perpendicular to that surface. Twenty-two attrition media cylinders of 3.2 cm×3.2 cm (19), made of zirconia or alumina (purchased from E. R. Advanced Ceramics, East Palestine, Ohio), are added to the reaction vessel occupying about 5.5% of the vessel volume. The apparatus is rotated at about 19 rpm during a treatment process by placing the apparatus on a roller support (20; Bellco Cell Production Roller Apparatus, Bellco Technology, Vineland, N.J., USA), to form the biomass processing system. The roller support and apparatus are placed inside an incubator chamber (23) for temperature control.

External equipment is attached to the apparatus of FIG. 2 to form a system, as in the following examples. For introduction of pretreatment reactant, an HPLC pump capable of approximately 800 ml/min flow rate at 10342 kPa gauge pressure is connected to the branched injection lance port rotary connector in the cover. The HPLC pump is connected through a heating coil constructed from 0.32 cm stainless steel tubing that is immersed in water in an 8 L Parr reactor vessel. The Parr reactor heater controller is set above the boiling point of water in Golden, Colo. (about 93° C.) with a heater input of 3 kW to maintain a rapid boil. A vacuum source is attached to the branched injection lance port rotary connector in the cover. The vacuum source may be connected to a vent condenser that is connected to a chilled water bath operating at about 1.5° C. The vent condenser includes a Teflon™ coated 2 L flask that is immersed in an ice-water bath and is connected to a vacuum manifold evacuated to about 85 kPa. A $CO_2$ source may also be connected to the branched injection lance port rotary connector.

It will be understood that the system including the apparatus may be scaled up, based on the features and principles described herein. An apparatus having a reaction vessel that is approximately 3-4 meters in diameter and about 15-18 meters in length is particularly suitable for commercial scale biomass treatment. Apparatuses with reaction vessels of sizes intermediate to that described in FIG. 2 and this commercial scale size are also embodiments of the present apparatus.

Methods of Apparatus Use in Biomass Treatment

The present system is designed for treatment of biomass, including different types of treatment using different processes. In one embodiment the system is used in a biomass pretreatment process. In another embodiment the system is used in a biomass saccharification process. These two types of biomass treatment may be carried out successively on the same biomass sample, or individually on different biomass samples. A biomass sample may be pretreated in another apparatus and saccharified in the apparatus of the present system, or a biomass sample may be pretreated in the present apparatus and then saccharified in a separate apparatus.

The present system including the apparatus is particularly suited to treatment of biomass, and particularly for saccharification of biomass, at a high dry weight of biomass in the biomass-reactant mixture. The initial dry weight of biomass may be up to about 80% of the weight of the biomass-reactant mixture. More suitably, the dry weight of biomass is up to about 60% of the weight of the biomass-reactant mixture. Preferred is an initial biomass concentration that is between about 15% and about 50% of the weight of the biomass-reactant mixture. The introduction of reactant through the injection lance, and the functioning of the attrition media and baffles provide assimilation of the reactant into the biomass, such that processing at high biomass concentrations is effective. In the context of saccharification, where enzymes such as cellulases and hemicellulases hydrolyze the biomass to produce fermentable sugars, the enzymes are assimilated into the biomass in the mixture by the cascading of the biomass and attrition media by the rotating baffles of the vessel. The effects of the cascading media on the biomass allow the treatment of biomass at a high dry weight of biomass in the biomass mixture.

In a pretreatment process, biomass is introduced into the present apparatus through the open end of the reaction vessel. Prior to introducing the biomass into the apparatus, energy may be applied to the biomass to reduce the size and/or increase the exposed surface area, such as by crushing, milling, grinding, shredding, chopping, disc refining, ultrasound, and microwave. The amount of biomass introduced depends on the size of the reaction vessel and the particular treatment process to be used, and can be determined by one skilled in the art. The apparatus may be preheated to a desired processing temperature.

A processing reactant is injected through a port in the secured vessel cover, and through the injection lance into the reaction vessel. In one embodiment the reactant is preheated and is introduced by spraying through holes in the upper surface of the injection lance while the baffles rotate such that the reactant contacts the biomass as it passes above the spray. The processing reactant may be any composition that is used in a biomass pretreatment process and that is compatible with the material from which the apparatus is constructed. Typical pretreatment reactants include oxidizing agents, denaturants, detergents, organic solvents, and bases, lists of which are provided in US2004/0231060, as well as acids. Some suitable reactants include peracetic acid (Teixeira et al. (1999) Appl. Biochem. and Biotech. 77-79:19-34), hydrogen peroxide (Gould (1983) Biotech. and Bioeng. 26:46-52), sodium hydroxide and hydrogen peroxide (Curreli et al. (2002) Process Biochem. 37:937-941), aqueous ammonia (Kim and Lee (2005) Bioresource Tech. 96:2007-2013), and liquid anhydrous ammonia (Teymouri et al. (2005) Bioresource Tech. 96:2014-2018). A particularly suitable processing reactant for biomass pretreatment in the present apparatus is aqueous ammonia. Most preferred is an aqueous solution comprising ammonia used in a biomass-aqueous ammonia mixture wherein the ammonia is present at a concentration at least sufficient to maintain alkaline pH of the biomass-aqueous ammonia mixture, but wherein the ammonia is present at less than about 12 weight percent relative to dry weight of biomass, as described in co-pending application CL2825.

The amount of process reactant added, and therefore the biomass concentration, may vary depending on the pretreatment process used. Particularly suitable in the present apparatus is pretreatment at a high concentration of biomass, where the dry weight of biomass is at an initial concentration of at least about 15 weight percent relative to the weight of the biomass-aqueous ammonia mixture. The high biomass concentration reduces the total volume of pretreated material, making the process more economical. In addition, with high biomass concentration, the need for concentration of sugars following saccharification of the pretreated biomass to allow high titers in fermentation, is minimized. The squeezing and infiltrating mode of mechanical mixing in the present apparatus, described above, is particularly suitable for a biomass treatment process at a high dry weight of biomass in the biomass mixture.

Prior to loading biomass into the present apparatus, the atmosphere in the reactor vessel may be flushed with nitrogen or any other gas of choice. For example, a vacuum is pulled and $N_2$ is introduced through a port to replace the air. This may be repeated as many times as needed to substantially replace the air.

The apparatus containing the biomass and pretreatment reactant is temperature controlled, as described herein above. The baffles of the reaction vessel are rotated, as described herein above. The amount of time allowed for the pretreatment process depends on the specific process being used and typically varies between about 5 minutes and about 8 hours. As the reaction is run, samples may be taken from a port in the cover of the apparatus. These samples may be analyzed to assess completeness of the pretreatment reaction. Various analytical methods may be used depending on the pretreatment process being used, for example, near infrared (NIR) spectroscopy, full chemical analysis or by running a small saccharification on a sample.

When using a reactant that forms a vapor under the pretreatment conditions, the reactant vapor may be collected by applying a vacuum attached to a vent condenser, as described herein above. Typically, after the pretreatment process is complete, the reactant vapor is collected and condensed so that it may be reused. An example is the collection of ammonia vapor when using liquid ammonia as a reactant. The collected ammonia vapor may be liquefied and used in the process reactant for pretreating additional biomass.

Pretreated biomass may be removed from the apparatus, or the second type of biomass treatment, saccharification, may be performed without removing the pretreated biomass. Alternatively, a biomass sample that has been pretreated in a separate apparatus may be introduced into the present apparatus for saccharification treatment. The amount of saccharification reactant added, and therefore the biomass concentration, may vary depending on the saccharification process used. The saccharification reactant is typically injected directly into the reaction vessel using the injection lance of the present apparatus. The introduction of saccharification reactant through the injection lance, and the functioning of the attrition media and baffles promote assimilation of the reactant into the biomass, such that saccharification at high biomass concentrations is effective. A saccharification reactant may be introduced through a port in the cover, or into the vessel with the cover opened, in a dry form.

The dry weight of biomass during saccharification may be up to about 80% of the weight of the biomass-reactant mixture. More suitably, the dry weight of biomass is up to about 60% of the weight of the biomass-reactant mixture. Preferred is an initial biomass concentration that is between about 15% and about 40% of the weight of the biomass-reactant mixture. The high biomass concentration reduces the total volume of saccharified material, making the process more economical. It demonstrates the effectiveness of the saccharification enzyme consortium under high biomass content where the levels of impurities, starting substrates and products are not diluted, where various inhibition and deactivation processes could take place. At low biomass concentration, as typically used in saccharification, the potential inhibition and deactivation processes are significantly diminished or non-existent due to the high dilution factor. In addition, with high biomass concentration the need for concentration of sugars following saccharification, to produce high titers in fermentation, is minimized. The squeezing and infiltrating mode of mechanical mixing in the present apparatus, described above, is particularly suitable for saccharification at a high dry weight of biomass in the biomass mixture.

The saccharification processing reactant comprises enzymes that are able to hydrolyze the pretreated biomass to release oligosaccharides and/or monosaccharides. Saccharification enzymes and methods for biomass treatment with saccharification enzymes are reviewed in Lynd, L. R., et al. (Microbiol. Mol. Biol. Rev. (2002) 66:506-577).

Typically a saccharification enzyme consortium is used, which comprises one or more enzymes selected primarily, but not exclusively, from the group "glycosidases" which hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem. (1994) 223:1-5, Eur. J. Biochem. (1995) 232:1-6, Eur. J. Biochem. (1996) 237:1-5, Eur. J. Biochem. (1997) 250:1-6, and Eur. J. Biochem. (1999) 264:610-650, respectively]) of the general group "hydrolases" (EC 3.). Glycosidases useful in the present process can be categorized by the biomass component that they hydrolyze. Glycosidases useful for the present process include cellulose-hydrolyzing glycosidases (for example, cellulases, endoglucanases, exoglucanases, cellobiohydrolases, β-glucosidases), hemicellulose-hydrolyzing glycosidases (for example, xylanases, endoxylanases, exoxylanases, β xylosidases, arabinoxylanases, mannases, galactases, pectinases, glucuronidases), and starch-hydrolyzing glycosidases (for example, amylases, α-amylases, β-amylases, glucoamylases, α-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), and feruloyl esterases (EC 3.1.1.73) to help release polysaccharides from other components of the biomass. It is well known in the art that microorganisms that produce polysaccharide-hydrolyzing enzymes often exhibit an activity, such as cellulose degradation, that is catalyzed by several enzymes or a group of enzymes having different substrate specificities. Thus, a "cellulase" from a microorganism may comprise a group of enzymes, all of which may contribute to the cellulose-degrading activity. Commercial or non-commercial enzyme preparations, such as cellulase, may comprise numerous enzymes depending on the purification scheme utilized to obtain the enzyme. Thus the saccharification enzyme consortium of the present process may comprise enzyme activity, such as "cellulase", however it is recognized that this activity may be catalyzed by more than one enzyme. Saccharification enzymes may be obtained commercially, such as Spezyme® CP cellulase (Genencor International, Rochester, N.Y.) and Multifect® xylanase (Genencor).

One skilled in the art will know how to determine the effective amount of enzymes to use in the consortium and adjust conditions for optimal enzyme activity. One skilled in the art would also know how to optimize the classes of enzyme activities required within the consortium to obtain optimal saccharification of a given pretreated biomass under the selected conditions.

When pretreating and then saccharifying biomass in the present apparatus, prior to saccharification treatment, the pH and temperature of the pretreated biomass in the present apparatus are adjusted to be favorable for activity of the saccharification enzymes to be used. When pretreating with an acid or base, the pH of the pretreated biomass may be either raised or lowered, respectively, by introduction of a pH adjusting solution or solid to the reaction vessel. For good distribution of a pH adjusting solution in the pretreated biomass, it is injected through the lance while the baffles in the reaction vessel are rotating. The solution may be prewarmed, typically to a temperature compatible with the saccharification enzyme consortium, such as to about 50° C. Alternatively, a pH adjusting solution may be introduced through a port in the cover. The baffles of the vessel may be rotated to promote assimilation of the pH adjusting solution into the biomass provided by the attrition media and baffles, and the biomass periodically tested by removing a sample through the sample port for pH testing until the desired pH is achieved. The target pH may be between about 2 and 11, depending on the enzymes being used for saccharification, since different enzymes may exhibit different pH optima as is known by one skilled in the art. More typically the desired pH is between about 4 and 10, with a pH of about 5.5 being most typical.

The temperature for saccharification is generally in a range between about 15° C. to about 100° C., also depending on the enzymes being used for saccharification, since different enzymes may exhibit different temperature optima as is known by one skilled in the art. Typically the temperature is between about 20° C. and about 100° C. Saccharification is performed while the baffles of the reaction vessel rotate. The squeezing and infiltrating mode of assimilating the reactant into the biomass in the present apparatus, described herein above, enhances access of the saccharification reactant to the biomass, thereby providing a highly effective saccharification process. This process is run for a time of about several minutes to about 120 hours, and preferably from about several hours to about 72 hours. The time for the reaction will depend on enzyme concentration and specific activity, as well as the substrate used and the environmental conditions, such as temperature and pH. One skilled in the art can readily determine optimal conditions of temperature, pH and time to be used with a particular biomass substrate and saccharification enzyme consortium.

The present apparatus is particularly useful for optimizing biomass treatment processes. There are many treatment conditions that may be varied in a biomass treatment process, whether it is a pretreatment or a saccharification process. Variable conditions include but are not limited to, pH, temperature, types of processing reactants and concentrations of processing reactants, percent dry weight of biomass in the biomass-reactant mixture, feed strategies for adding reactants, pressures, type of inert atmosphere, form and type and form of biomass used, and process time. The present apparatus may be constructed on a small scale, as described in one embodiment herein above (shown in FIG. 2), that is particularly suitable for optimizing treatment conditions. The conditions may be independently varied or varied in parallel using statistical design of experimentation and samples taken from the sample port while the process is run. In a saccharification process, or a combined pretreatment/saccharification process, sugars in the samples may be directly analyzed. In a pretreatment process alone, samples are saccharified and then the saccharification product is analyzed for sugar content and other components of interest, such as acetic acid, furfurals, and salts. Other methods also may be used for analysis, such as for hemicellulose. Optimization may be based on a number of criteria, including sugar monomer yield, total released sugar yield, low enzyme usage, low acetic acid, low fufurals, low impurities formed, or a global optimization based on several of these variables. For example, the percentages of glucose and xylose theoretically present in the starting biomass that are released in the treatment process being assessed, is determined. Sugar monomer yields near or above 50% indicate good results, with even higher yields being preferred. Total sugar yields, including released oligomers, of at least 70% indicate good yields. Methods for analysis of the sugars are well known to one skilled in the art, such as by HPLC. In addition, other treated biomass sample components may be analyzed, also by HPLC, such as acetic acid, furfurals, or lactic acid, in assessing the quality of the product.

Fermentable sugars released from biomass can be used by suitable microorganisms, which are biocatalysts, to produce target chemicals, such as described in co-pending US patent applications CL3435 and CL3436.

EXAMPLES

General Methods and Materials

The following abbreviations are used:

"HPLC" is High Performance Liquid Chromatography, "C" is Centigrade, "kPa" is kiloPascal, "m" is meter, "mm" is millimeter, "kW" is kilowatt, "µm" is micrometer, "µL" is microliter, "mL" is milliliter, "L" is liter, "min" is minute, "mM" is millimolar, "cm" is centimeter, "g" is gram, "kg" is kilogram, "wt" is weight, "hr" is hour, "temp" or "T" is temperature, "theoret" is theoretical, "pretreat" is pretreatment, "DWB" is dry weight of biomass. Sulfuric acid, ammonium hydroxide, acetic acid, acetamide, yeast extract, 2-morpholinoethanesulfonic acid (MES), potassium phosphate, glucose, xylose, tryptone, sodium chloride and citric acid were obtained from Sigma-Aldrich (St. Louis, Mo.).

Pretreatment and Enzymatic Hydrolysis Reactor (PEHR)

A biomass treatment apparatus with dimensions and features as shown in FIG. 2 and described herein above is called the PEHReactor and was used in the following Examples. Briefly, the 9L PEHReactor (constructed at NREL, Golden, Colo.) has an approximately 15 cm×51 cm stainless steel reaction vessel with an injection lance for introduction of processing reactants. The injection lance is connected using a rotary joint to a port in a cover on one end of the vessel, which has an additional port for vessel access. Four baffles run the length of the vessel wall, and are attached perpendicularly to the wall. The baffles and twenty-two ceramic attrition media cylinders of 3.2 cm×3.2 cm (E. R. Advanced Ceramics, East Palestine, Ohio), free floating in the vessel, apply mechanical mixing of biomass and reactant as the vessel is rotated, promoting assimilation of reactant into the biomass. The PEHReactor is placed on a Bellco Cell-Production Roller Apparatus (Bellco Technology, Vineland, N.J.) which provides a mechanism for rotation, and the reactor with roller apparatus is housed in a temperature controlled chamber which provides heat. The temperature controlled chamber consists of an aluminum frame to support cork insulating pads surrounding the Bellco Cell Production Apparatus, to which a heater is attached that is controlled by thermocouples inserted through the center of the injection lance in the PEHReactor. Vacuum and pressure may be applied to the reaction vessel by attaching external sources to the lance-connected port in the cover.

Steam Gun Reactor Batch Digestion System

The 4-liter steam gun reactor (Autoclave Engineers, Erie, Pa.) is a steam-jacketed reactor consisting of a length of 102 mm schedule 80 Hastelloy® pipe closed by two ball valves. Additional electrical heaters are placed on all exposed, non-jacketed surfaces of the reactor and controlled to the pretreatment set point temperature. Direct steam injection is also used to rapidly bring the biomass up to pretreatment temperature. Steam pressure is adjusted and controlled to maintain the desired pretreatment temperature. The bottom of the reactor is necked down to 51 mm. All pretreated material exits through a replaceable die at the bottom of the reactor and is collected in a nylon (Hotfill®) 0.21 $m^3$ bag supported within a heavy walled, jacketed, and cooled flash tank.

Analytical Methods

Measurement of Sugar, Acetamide, Lactic Acid and Acetic Acid Content

Soluble sugars (glucose, cellobiose, xylose, galactose, arabinose and mannose), acetamide, lactic acid and acetic acid in saccharification liquor were measured by HPLC (Agilent Model 1100, Agilent Technologies, Palo Alto, Calif.) using Bio-Rad HPX-87P and Bio-Rad HPX-87H columns (Bio-Rad Laboratories, Hercules, Calif.) with an appropriate guard columns. The sample pH was measured and adjusted to 5-6 with sulfuric acid if necessary. The sample was then passed through a 0.2 µm syringe filter directly into an HPLC vial. The HPLC run conditions were as follows:

HPX-87P (for carbohydrates):
- Injection volume: 10-50 µL, dependent on concentration and detector limits
- Mobile phase: HPLC grade water, 0.2 µm filtered and degassed
- Flow rate: 0.6 mL/minute
- Column temperature: 80-85° C., guard column temperature <60° C.
- Detector temperature: as close to main column temperature as possible
- Detector: refractive index
- Run time: 35 minute data collection plus 15 minute post run (with possible adjustment for later eluting compounds)

Biorad Aminex HPX-87H (for carbohydrates, acetamide, lactic acid and acetic acid)
- Injection volume: 5-10 µL, dependent on concentration and detector limits
- Mobile phase: 0.01N Sulfuric acid, 0.2 µm filtered and degassed
- Flow rate: 0.6 mL/minute
- Column temperature: 55° C.
- Detector temperature: as close to column temperature as possible
- Detector: refractive index
- Run time: 25-75 minute data collection After the run, concentrations in the sample were determined from standard curves for each of the compounds.

Example 1

Saccharification of Bagasse at High Biomass Concentration in the PEHReactor; Comparison to Low Concentration Saccharification The PEHReactor (described in General Methods), with no attrition media, was charged with 1.27 cm-milled bagasse (370 g, dry weight basis). This sugar cane bagasse was NIST Reference Material RM8491, from sugar cane clone H65-7052, originally obtained from the Hawaii Sugar Planters Association, Kunia substation, Oahu, Hi. It was milled in a Wiley mill to pass through a 2 mm screen, with the fines (+74 mesh) removed. The reactor vessel was cooled to 4° C. by rotation in contact with ice on the outer surface. A vacuum was applied to the reactor vessel, and dilute ammonium hydroxide solution, that was pre-cooled in a cold room at 4° C. and passed through tubing immersed in an ice-water bath, was injected to give an ammonia concentration of 4 g/100 g dry weight of biomass and a dry weight of biomass concentration of 45 g/100 g total biomass-aqueous ammonia mixture. The reactor vessel charged with ammonia and bagasse was cooled to 4° C. by applying ice to the surface of the rotating reactor vessel, and rotated at 4° C. for 30 min. At this time the contents were transferred to the steam gun reactor that is described in General Methods. Once the steam gun reactor was charged with the ammonia-bagasse mixture, the temperature was increased to 145° C. and the mixture was held at temperature for 20 minutes. At the end of the pretreatment time, the bagasse was discharged from the steam gun reactor through a 2.54 cm circular die into a flash tank. A sample of pretreated bagasse was subsequently saccharified in a shake flask and another sample (approximately 163 g dry weight) was saccharified in the PEHReactor. The shake flask saccharification was carried out at 5% dry weight of biomass relative to the total weight of the pretreated biomass-saccharification enzyme consortium mixture, while the PEHReactor saccharification was carried out at 30% dry weight of biomass relative to the total weight of the pretreated biomass-saccharification enzyme consortium mixture. The pH was controlled at 5.5 during saccharification by the addition of 50 mM citrate buffer, and the temperature was maintained at 50° C.

For the PEHReactor saccharification, about 476 g (~163 g dry weight) pretreated biomass and 22 ceramic attrition cylinders were added to the reactor vessel. The pH was adjusted to 5.0-5.5 with solid citric acid. The reactor vessel was kept inside an incubator chamber controlled to 50° C. and rotated axially at 19 rpm. Unpretreated bagasse was also saccharified at 5% dry weight of biomass relative to the total weight of the pretreated biomass-saccharification enzyme consortium mixture in a shake flask. All saccharifications were done with 28.4 mg/g cellulose Spezyme CP® cellulase and 28.4 mg/g cellulose Multifect® xylanase at 50° C. and pH 5.5 for 96 hr. Yields given in Table 1 below are the release as percent of theoretical yield.

TABLE 1

Yields following pretreatment and saccharification of bagasse.

| | No pretreatment 5% saccharification | Pretreated 5% DWB saccharification | Pretreated 30% DWB saccharification |
|---|---|---|---|
| Monomer glucose | 0.5% | 16.6% | 23.3% |
| Total glucose | ND | ND | 36.4% |
| Monomer xylose | 1.3% | 15.6% | 17.2% |
| Total xylose | ND | ND | 37.4% |

ND: not determined

The results demonstrate that pretreatment of bagasse with very low ammonia allows substantial sugar release as compared to the unpretreated control, and that saccharification at high solids concentration in the PEHReactor is very effective in releasing sugars.

Example 2

Saccharification of Yellow Poplar Sawdust at High Biomass Concentration in the PEHReactor; Comparison to Low Concentration Saccharification The PEHReactor, without attrition media, was charged with yellow poplar sawdust (596 g, dry weight basis; purchased from Sawmiller Inc., Haydenville, Ohio). A vacuum was applied to the reactor vessel, and dilute ammonium hydroxide solution was injected to give an ammonia concentration of 6 g/100 g dry weight of biomass and a dry weight of biomass concentration of 44 g/100 g total biomass-aqueous ammonia mixture. The reactor vessel charged with ammonia and yellow poplar sawdust was brought to 4° C. as described in Example 1, and rotated at 4° C. for 30 min. At this time the contents were transferred to the steam gun reactor. Once the steam gun reactor was charged with the ammonia-poplar mixture, the temperature was increased to 145° C. and the mixture was held at temperature for 20 minutes. At the end of the pretreatment time, the yellow poplar sawdust was discharged from the steam gun reactor through a 2.54 cm circular die into a flash tank. A sample of pretreated yellow poplar sawdust was subsequently saccharified as described in Example 1 in a shake flask, and another sample was saccharified in the PEHReactor. The shake flask saccharification was carried out at 5% dry weight of biomass relative to the total weight of the pretreated biomass-saccharification enzyme consortium mixture, while the PEHReactor saccharification (using ~279 g dry weight pretreated sawdust) was carried out at 30% dry weight of biomass relative to the total weight of the pretreated biomass-saccharification enzyme consortium mixture. Unpretreated yellow poplar sawdust was also saccharified at 5% dry weight of biomass relative to the total weight of the pretreated biomass-saccharification enzyme consortium mixture in a shake flask. All saccharifications were done with 28.4 mg/g cellulose Spezyme CP® cellulase and 28.4 mg/g cellulose Multifect® xylanase at 50° C. and pH 5.5 for 96 hr. Yields given in the Table 2 below are the release as percent of theoretical yield.

TABLE 2

Yields following pretreatment and saccharification of yellow poplar sawdust.

| Component | No pretreatment 5% DWB saccharification | Pretreated 5% DWB saccharification | Pretreated 30% DWB saccharification |
|---|---|---|---|
| Monomer glucose | 2.7% | 11.1% | 20.6% |
| Total glucose | ND | ND | 30.0% |
| Monomer xylose | 0% | 17.9% | 18.9% |
| Total xylose | ND | ND | 40.2% |

ND: not determined

The results demonstrate that pretreatment of yellow poplar sawdust with very low ammonia allows substantial sugar release as compared to the unpretreated control, and that saccharification at high dry weight of biomass in the PEHReactor is more effective in releasing sugars than the shake flask.

Example 3

Pretreatment and Saccharification of Corn Cobs at Higher Dry Biomass Concentration in PEHReactor Whole corn cobs were processed with a jaw crusher (2.2 kW motor) with a jaw spacing of approximately 0.95 cm, followed by a delumper (1.5 kW motor, Franklin Miller Inc., Livingston, N.J.), followed by screening with a Sweco screen equipped with a 1.9 cm U.S. Standard screen. Approximately 805 g fractured cobs were loaded into the PEHReactor. Moisture content in the cobs was approximately 7%. The atmosphere in the reactor vessel was flushed 5 times with nitrogen prior to loading. The reactor, with no attrition media, was preheated to 75° C. before the start of the experiment, without rotation. When the temperature within the reactor vessel stabilized at 75° C. the rolling mechanism in the incubator was turned on and the rotation adjusted to 19 rpm. The appropriate amount of dilute ammonium hydroxide solution to give an ammonia concentration of 6 g ammonia/100 g dry weight of biomass and a solids concentration of 50 g dry weight of biomass/100 g total weight of biomass-ammonia mixture was then pumped into the reactor. Ethanol at 1 g/100 g dry weight of biomass was also added to the solution. The ammonia solution was pumped through a heated loop in a water bath at ~75° C. fabricated using a 2-gal Parr reactor. The heated dilute ammonium hydroxide solution was injected via an injection lance into the reactor vessel and sprayed on the fractured cobs rotating and tumbling in the reactor. The reactor was maintained at 75° C. for 2 hr while turning at 19 rpm. At the end of that time, a vacuum (approximately 85 kPa) was applied to the reactor vessel for 30 minutes to remove ammonia and drop the temperature of the contents of the reactor to approximately 50° C. Carbon dioxide was then injected into the reactor to relieve the vacuum and the reactor was pressurized to 103 kPa gauge pressure and held at pressure for 30 min at 50° C.

Following this, the reactor was depressurized, opened and attrition media were added. The pH of the contents was adjusted to approximately 5.5 by injecting 1 M citric acid buffer at pH 4.8 using the injection lance, to increase the citric acid buffer strength to ~75 mM, plus adding citric acid monohydrate. The citric acid buffer was injected into the reactor following heating to 50° C. and then the contents was allowed to equilibrate by incubating the reactor at 50° C. and 19 rpm for 1 hour. Injection of the citric acid buffer while rotating the reactor using the injection lance allowed for a more even spraying and distribution of the buffer on the pretreated cob particles. The reactor was removed from the incubator, opened, and the pH of a sample determined. If the pH was above 5.5, then additional solid citric acid monohydrate was added and the reactor was incubated with mixing at 50° C. for an additional hour. This process was repeated until the pH was approximately 5.5. Once the desired pH was reached, 12.9 mg/g cellulose Spezyme CP (Genencor) and 5 mg active protein/g cellulose enzyme consortium consisting of -glucosidase, xylanase, -xylosidase and arabinofuranosidase were loaded into the reactor. The reactor remained in the incubator at 50° C. and 19 rpm for 72 hr. Following this pretreatment and saccharification, monomer glucose yield was 62.0% and monomer xylose yield was 31.0%. Total glucose yield was 75.2% and total xylose yield was 80.3%.

Example 4

Cob Pretreatment at Higher Biomass Concentration with Very Low Ammonia and Alternate Conditions Whole corn cobs were processed with a hammermill (10-inch hammer mill, Glen Mills Inc., Clifton, N.H.) to pass through a 1.27 cm screen. Approximately 805 g fractured cobs were loaded into the PEHReactor. Moisture content in the cobs was approximately 7%. Twenty-two ceramic attrition cylinders (3.2 cm diameter×3.2 cm long; E. R. Advanced Ceramics, East Palestine, Ohio) were also added to the reactor. The reactor was preheated to 95° C. before the start of the experiment, without rotation. A vacuum (approximately 85 kPa) was applied to the reactor vessel before the start and the vessel was sealed off. When the temperature within the reactor vessel stabilized at 95° C. the rolling mechanism in the incubator was turned on and the rotation adjusted to 19 rpm. The appropriate amount dilute ammonium hydroxide solution to give an ammonia concentration of 6 g ammonia/100 g dry weight of biomass and a solids concentration of 50 g dry weight of biomass/100 g total weight of biomass-ammonia mixture was then pumped into the reactor. The ammonia solution was pumped through a heated loop in a boiling water bath fabricated using a 2-gal Parr reactor. The heated dilute ammonium hydroxide solution was injected via an injection lance into the reactor vessel and sprayed on the fractured cobs rotating and tumbling in the reactor. The reactor was maintained at 95° C. for 2 hr while turning at 19 rpm. At the end of that time, a vacuum (approximately 85 kPa) was applied to the reactor vessel for 30 minutes to remove ammonia and drop the temperature of the contents of the reactor to approximately 50° C. Carbon dioxide was then injected into the reactor to relieve the vacuum and the reactor was pressurized to 103 kPa gauge pressure and held at pressure for 30 min at 50° C.

Following this, the reactor was depressurized, opened and the pH of the contents was adjusted to approximately 5.5 by injecting 1 M citric acid buffer, pH 4.8, into which citric acid monohydrate was added and dissolved. The citric acid buffer was injected into the reactor following heating to 50° C. and then the contents was allowed to equilibrate by incubating the reactor at 50° C. and 19 rpm for 1 hour. The reactor was removed from the incubator, opened, and the pH of a sample determined. If the pH was above 5.5, then additional solid citric acid monohydrate was added and the reactor was incubated with mixing at 50° C. for an additional hour. This process was repeated until the pH was approximately 5.5. Once the desired pH was reached, 12.9 mg/g cellulose Spezyme CP (Genencor) and 5 mg active protein/g cellulose enzyme consortium consisting of -glucosidase, xylanase, -xylosidase and arabinofuranosidase were loaded into the reactor. The reactor remained in the incubator at 50° C. and 19 rpm for 72 hr. Following this pretreatment and saccharification, monomer glucose yield was 50.7% and monomer xylose yield was 35.7%. Total glucose and xylose yields were 71.7% and 89.8%, respectively.

Example 5

Pretreatment of Cobs with Very Low Ammonia and Additional Base

Whole corn cobs were processed with a jaw crusher (2.2 kW motor) with a jaw spacing of approximately 0.95 cm, followed by a delumper (1.5 kW motor, Franklin Miller Inc.), followed by screening with a Sweco screen equipped with a 1.9 cm U.S. Standard screen. Approximately 460 g fractured cobs were loaded into the PEHReactor. Moisture content in the cobs was approximately 7%. The reactor was preheated to 95° C. before the start of the experiment, without rotation. A vacuum (approximately 85 kPa) was applied to the reactor vessel before the start and the vessel was sealed off. When the temperature within the vessel re-stabilized at 95° C. the rolling mechanism in the incubator was turned on and the rotation was adjusted to 19 rpm. The appropriate amount of ammonium hydroxide solution to give an ammonia concentration of 3.2 g ammonia/100 g dry weight of biomass and NaOH to give a concentration of 1.9 g NaOH/100 g dry weight of biomass while maintaining a solids concentration of 30 g dry weight of biomass/100 g total weight of biomass-ammonia mixture was then pumped into the reactor. The ammonia and additional base solution was pumped through a heated loop in a boiling water bath fabricated using a 2-gal Parr reactor. The heated dilute ammonium hydroxide solution was injected via an injection lance into the reactor vessel and sprayed on the fractured cobs rotating and tumbling in the reactor. Following injection, the vacuum on the vessel was relieved to atmospheric pressure. The reactor was maintained at 95° C. 30 min, then the temperature was lowered to 85° C. where it was maintained for 4 hr. At the end of that time, a vacuum (approximately 85 kPa) was applied to the reaction vessel for 30 minutes to remove ammonia and drop the temperature of the contents of the reactor to approximately 50° C. Carbon dioxide was then injected into the reactor to relieve the vacuum and the reactor was pressurized to 103 kPa gauge pressure and held at pressure for 30 min at 50° C.

Following this, the reactor was depressurized, opened and the pH of the contents was adjusted to approximately 5.5 by injecting approximately 75 ml of 1 M citric acid buffer, pH 4.8, into which citric acid monohydrate was added and dissolved. The citric acid buffer was injected into the reactor following heating to 50° C. and the contents was then allowed to equilibrate by incubating the reactor at 50° C. and 19 rpm for 1 hour. Injection of the citric acid buffer while rotating the reactor using the injection lance allowed for a more even spraying and distribution of the buffer on the pretreated cob particles. The reactor was removed from the incubator, opened, and the pH of a sample determined. If the pH was above 5.5, then additional solid citric acid monohydrate was added and the reactor was incubated with mixing at 50° C. for an additional hour. This process was repeated until the pH was approximately 5.5. Once the desired pH was reached, 28.4 mg/g cellulose Spezyme CP (Genencor) and 28.4 mg/g cellulose Multifect were loaded into the reactor. The reactor remained in the incubator at 50° C. and 19 rpm for 72 hr. Following this pretreatment and saccharification, monomer glucose yield was 56.1% and monomer xylose yield was 39.5%. Total glucose and xylose yields were 82.8% and 84.2%, respectively. These values are the averages of 2 experiments.

Example 6

Pretreatment and Saccharification of Corm Cobs at High Dry Biomass Concentration in PEHReactor at Room Temperature Whole corn cobs were processed with a jaw crusher (2.2 kW motor) with a jaw spacing of approximately 0.95 cm, followed by a delumper (1.5 kW motor, Franklin Miller Inc.), followed by screening with a Sweco screen equipped with a 1.9 cm U.S. Standard screen. Approximately 460 g fractured cobs were loaded into the PEHReactor. Moisture content in the cobs was approximately 7%. Twenty-two ceramic attrition cylinders (3.2 cm diameter×3.2 cm long; E. R. Advanced Ceramics, East Palestine, Ohio) were also added to the reactor. A vacuum (approximately 85 kPa) was applied to the reactor vessel before the start and the vessel was sealed off. When the temperature within the reactor re-stabilized at room temperature (22-26° C.) the rolling mechanism in the incubator was turned on and rotation was adjusted to 19 rpm. The appropriate amount of dilute ammonium hydroxide solution to give an ammonia concentration of 4 g ammonia/100 g dry weight of biomass and while maintaining a solids concentration of 30 g dry weight of biomass/total weight of biomass-ammonia mixture was then pumped into the reactor. The dilute ammonium hydroxide solution was injected via an injection lance into the reacter vessel and sprayed on the fractured cobs rotating and tumbling in the reactor. Following injection, the vacuum on each vessel was relieved to atmospheric pressure. The reactor was maintained at room temperature (22-26° C.) for 24 hr. At the end of that time, a vacuum (approximately 81 kPa) was applied to the reaction vessel for 30 minutes to remove ammonia. Carbon dioxide was then injected into the reactor to relieve the vacuum and the reactor was pressurized to 103 kPa gauge pressure with $CO_2$ and held at pressure for 30 min at room temperature.

Following this, the reactor was depressurized, opened and the pH of the contents was adjusted to approximately 5.5 by adding citric acid monohydrate. following heating to 50° C., and then allowed to equilibrate by incubating the reactor at 50° C. and 19 rpm. The reactor was removed from the incubator, opened, and the pH of a sample determined. If the pH was above 5.5, then additional solid citric acid monohydrate was added and the reactor was incubated with mixing at 50° C. This process was repeated until the pH was approximately 5.5. Once the desired pH was reached, 12.9 mg/g cellulose Spezyme CP (Genencor) and 5 mg active protein/g cellulose enzyme consortium consisting of -glucosidase, xylanase, -xylosidase and arabinofuranosidase were loaded into the reactor. The reactor remained in the incubator at 50° C. and 19 rpm for 72 hr. Following this pretreatment and saccharification, monomer glucose yield was 41.7% and the monomer xylose yield was 25.4%. Total glucose and xylose yields were 50.1% and 53.2%, respectively. These values were the averages of 2 experiments.

Example 7

Pretreatment and Saccharification of Combined Biomass Containing Corn Cobs and Different Spent Grain Samples in PEHReactor Spent grain samples were prepared from:
1. #2 yellow dent whole corn grain (purchased from Agway)
2. Corn grain degermed by the Quick Germ process developed at the University of Illinois (Singh and Eckoff (1996) Cereal Chem. 74: 462-466). Starting material was obtained from Vijay Singh at the University of Illinois.
3. Corn grain process by the Quick Fiber process to remove the germ and the hull fiber (U.S. Pat. No. 6,254,914). Starting material was obtained from Vijay Singh at the University of Illinois.
4. Brewers' grits were obtained from Cargill (Minneapolis, Minn.).

Spent grains refers to residual solids from grain processing in which starch is converted to sugar. Spent grains were produced essentially by a basic whiskey process. The different starting materials were treated with starch-degrading enzymes to produce sugars, and the resulting mash was filtered to retrieve the filter cake solids, or spent grains.

The starting materials were ground in a Foss (North American HQ: Eden Prarie, Minn.) Cyclotec 1093 sample mill (starting materials 1 and 2 above) to 250 μm or in a blender (starting materials 3 and 4 above), then combined with water and 200 mM CaCl2*H2O in a 2 L jacketed, stirred, glass reaction vessel. The pH of the mixture was adjusted to 6.5 with 1 N NaOH, and half of the total α-amylase (Spezyme HPA, Genencor International, Palo Alto, Calif.) was added. The reaction vessel was then heated to 95° C. and the remaining α-amylase was added 20 min later. After remaining at 95° C. for the specified time, the vessel was cooled to 70° C., and the pH of the mixture was adjusted to 4.5 with 1 M HCl. Glucoamylase (Gzyme 480, Genencor) was added, and the temperature was lowered further to 50° C. and held overnight. At this time, the reactor was cooled to <40° C., and the contents were filtered through Dacron filter cloth with a pore size of 10 μm. The filter cake was washed with water, and the final filter cake, or spent grains, was dried at 105° C. overnight and stored at room temperature until used in pretreatment experiments. Specific reaction conditions for each starting material are listed in the Table 3 below.

TABLE 3

Processing of spent grains samples.

| Starting material | Starting material added (g) | Water added (g) | α-amylase added (ml) | Total time at 95° C. | Gluco-amylase added (ml) | Time at 50° C. (hr) |
|---|---|---|---|---|---|---|
| 1 | 375 | 1095 | 3 | 150 | 3 | 17 |
| 2 | 505 | 1095 | 3 | 150 | 3 | 23 |
| 3 | 1180 | 500 | 6 | 120 | 3 | 17.5 |
| 4 | 1160 | 500 | 6 | 120 | 3 | 18 |

Whole corn cobs were processed with a jaw crusher (2.2 kW motor) with a jaw spacing of approximately 0.95 cm, followed by a delumper (1.5 kW motor, Franklin Miller Inc.), followed by screening with a Sweco screen equipped with a 1.9 cm U.S. Standard screen. Fractured cobs were loaded with one type of spent grain, as listed in Table 3, into a PEHReactor. Spent grains were approximately 10% of the total dry weight of biomass in the reactor. Total dry biomass charge was approximately 473 g. Each charged reactor was preheated in the roller incubator to 95° C., without rotation, before the start of the experiment. A vacuum (approximately 85 kPa gauge pressure) was applied to the reaction vessel and the vessel was sealed off. When the temperature within each reaction vessel re-stabilized at 95° C., rotation was started at 19 rpm. Dilute ammonium hydroxide solution was added to give an ammonia concentration of 4 g ammonia/100 g dry weight of biomass and a solids concentration of 30 g dry weight of biomass/100 g total weight of biomass-ammonia mixture. Following injection, the vacuum on the vessel was relieved to atmospheric pressure. The reactor was maintained at 95° C. for 30 min, then the temperature was lowered to 85° C. where it was maintained for 4 hr with rotation. At the end of that time, a vacuum (approximately 85 kPa gauge pressure) was applied to the reactor vessel for 30 minutes to remove ammonia and drop the temperature of the contents of each reactor to approximately 50° C. Carbon dioxide was then injected into each reactor to relieve the vacuum and the reactors were pressurized to 138 kPa gauge pressure with $CO_2$ and rotated at pressure for 30 min at 50° C.

Following this, the reactor was depressurized, opened and the pH of the contents was adjusted to approximately 5.5 by injecting 75 ml of 1 M citric acid buffer, pH 4.8, into which citric acid monohydrate was added and dissolved. The citric acid buffer was injected into each reactor following heating to 50° C. and then allowed to equilibrate by incubating the reactors at 50° C. and 19 rpm for 1 hour. The reactors were removed from the incubator, opened, and the pH of a sample determined. If the pH was above 5.5, then additional solid citric acid monohydrate was added and the reactors were incubated with rotation at 50° C. for an additional hour. This process was repeated as often as necessary to obtain a pH for each reactor of ~5.5. Once the desired pH was reached, 28.4 mg/g cellulose Spezyme® CP cellulase (Genencor) and 10.1 mg active protein/g cellulose of Diversa D2 cocktail containing a beta-glucosidase, xylanase, beta-xylosidase and arabinfuranosidase were loaded into the reactor. The reactors remained in the incubator at 50° C. and 19 rpm for 72 hr. Following this pretreatment and saccharification, sugar yields were assayed as described in General Methods. Glucose and xylose yields, based on total glucan and xylan coming in with both feeds, are shown in Table 4. Yields of the cob plus spent grain combination biomass samples were similar to yields of the cob alone sample.

TABLE 4

Sugar yields following pretreatment and saccharification of combined biomass feeds.

| | Monomer glucose | Total glucose yield | Monomer xylose yield | Total xylose yield |
|---|---|---|---|---|
| Cob only (avg of 2) | 68.2% | 85.6% | 41.8% | 88.9% |
| Cob + Quick Germ spent grains | 67.9% | 86.5% | 49.0% | 86.5% |
| Cob + Quick Fiber spent grains | 69.5% | 88.3% | 54.6% | 87.3% |
| Cob + Brewers Grits spent grains | 65.6% | 79.5% | 48.3% | 83.2% |

Example 8

Pretreatment and Saccharification of Combined Biomass Containing Corn Cobs, Spent Grain, and Additional Components in the PEHReactor Fractured cobs and whiskey spent grains, prepared as described in Example 7, were combined in the PEHReactor as described in Example 7. In addition, other grain components were added. In one sample, starch (Sigma S4126, lot #093K0033) was added at 5 g/100 g total dry weight of biomass. In another sample, corn oil (Sysco Classic corn oil, lot #4119095) was added at a level of about 2 g/100 g total dry biomass. The samples were pretreated and saccharified as described in Example 7. Results are shown in Table 4. These results also compare favorably with the cob only control data in Table 3.

TABLE 4

Sugar yields resulting from pretreatment and saccharification of cob, spent grains and additional grain components.

| | Monomer glucose | Total glucose yield | Monomer xylose yield | Total xylose yield |
|---|---|---|---|---|
| Cob + whiskey spent grains + starch | 70.4% | 90.2% | 48.4% | 96.1% |
| Cob + whiskey spent grains + oil | 79.2% | 87.5% | 54.9% | 101.4% |

Example 9

Pretreatment and Saccharification of Combined Biomass Containing Corn Cobs and Corn Fiber in the PEHReactor Fractured corn cobs and Cargill Bran 80 (Cargill, Minnetonka, Minn.) corn fiber were combined such that the fiber was approximately 10% of the total dry biomass. The combined biomass was pretreated and saccharified as described in Example 7. The resulting sugar yields are shown in Table 5.

Yields of the cob plus corn fiber combination biomass were similar to yields of the cob alone sample.

TABLE 5

Sugar yields resulting from pretreatment of corn cobs combined with corn fiber.

|  | Monomer glucose | Total glucose yield | Monomer xylose yield | Total xylose yield |
|---|---|---|---|---|
| Cob + Cargill Bran 80 | 66.4% | 82.3% | 47.0% | 83.5% |

We claim:

1. A process for pretreating biomass comprising:
   a) introducing biomass to a reaction vessel comprising:
      i) a cylindrical reaction vessel with an opening on at least one end;
      ii) one or more baffles attached to the interior of said vessel;
      iii) attrition media comprising pellets free-floating in the interior of the reaction vessel;
      iv) a cover for said vessel open end comprising one or more ports; and
      v) an injection lance comprising means for delivering processing reactants, wherein said means is an injection lance extending the length of the reaction vessel and connecting to a first port in the cover of iv);
   b) contacting said biomass with a process reactant comprising an aqueous solution comprising ammonia to form a biomass-aqueous ammonia mixture in the reaction vessel, wherein the ammonia is present at a concentration at least sufficient to maintain alkaline pH of the biomass-aqueous ammonia mixture but wherein said ammonia is present at less than 12 weight percent relative to dry weight of biomass, and further wherein the dry weight of biomass is at a solids concentration of at least 15 weight percent relative to the weight of the biomass-aqueous ammonia mixture; wherein said processing reactant is assimilated into said biomass by rotating the baffles of the reaction vessel whereby the baffles lift and drop the attrition media to produce a pretreated biomass.

2. A process for saccharifying pretreated biomass at dry biomass concentration, comprising:
   a) providing biomass, wherein said biomass has been pretreated to provide a readily saccharifiable composition according to process comprising contacting said biomass with a processing reactant comprising an aqueous solution comprising ammonia to form a biomass-aqueous ammonia mixture in the reaction vessel, wherein the ammonia is present at a concentration at least sufficient to maintain alkaline pH of the biomass-aqueous ammonia mixture but wherein said ammonia is present at less than 12 weight percent relative to dry weight of biomass, and further wherein the dry weight of biomass is at a high solids concentration of at least 15 weight percent relative to the weight of the biomass-aqueous ammonia mixture
   b) providing an enzyme consortium capable of hydrolyzing the pretreated biomass of (a);
   c) assimilating the enzymes of (b) into the biomass of (a) in an apparatus comprising:
      i) a cylindrical reaction vessel with an opening on at least one end;
      ii) one or more baffles attached to the interior of said vessel;
      iii) attrition media comprising pellets free-floating in the interior of the reaction vessel;
      iv) a cover for said vessel open end comprising one or more ports; and
      v) an injection lance comprising means for delivering processing reactants, wherein said means is an injection lance extending the length of the reaction vessel and connecting to a first port in the cover of iv) and wherein said enzymes are assimilated into said pretreated biomass by rotating the baffles of the reaction vessel whereby the baffles lift and drop the attrition media to produce a saccharified pretreated biomass.

3. The process of claim 2, wherein fermentable sugars are produced.

4. The process of claim 1 or 2, wherein said biomass is selected from the group consisting of switchgrass, waste paper, sludge from paper manufacture, corn grain, corn cobs, corn husks, corn stover, grasses, wheat, wheat straw, hay, barley, barley straw, rice straw, sugar cane bagasse, sorghum, soy, components obtained from processing of grains, trees, branches, roots, leaves, wood chips, sawdust, shrubs and bushes, vegetables, fruits, flowers and animal manure.

5. The process of claim 1 or 2, wherein said biomass is derived from multiple feedstocks.

6. The process of claim 1 comprising the additional steps of:
   c) adjusting the temperature and pH of the pretreated biomass of (b) in the reaction vessel; and
   d) saccharifying the adjusted pretreated biomass of (c) in the reaction vessel.

7. The process of claims 1 comprising the additional steps of:
   c) varying treatment conditions in the reaction vessel;
   d) sampling the treated biomass via said one or more ports under said varying treatment conditions; and
   e) testing said samples to determine optimal treatment conditions for processing biomass.

8. The process of claim 6 comprising the additional steps of:
   e) varying treatment conditions in the reaction vessel of step a);
   f) sampling the treated biomass via said one or more ports under said varying treatment conditions of step b); and
   g) testing said samples to determine optimal treatment conditions for processing biomass.

9. The process of claim 2 comprising the additional steps of:
   d) varying treatment conditions in the reaction vessel of step a);
   e) sampling the treated biomass via said one or more ports under said varying treatment conditions of step a); and
   f) testing said samples to determine optimal treatment conditions for processing biomass.

10. The method of any of claims 7, 8, or 9, wherein said varying conditions include, pH, temperature, processing reactants and concentrations of processing reactants, percent initial dry weight of biomass in the biomass-reactant mixture, type and form of biomass, type of inert atmosphere, pressure, feed strategies for process reactants, and processing time.

* * * * *